United States Patent [19]

Poncet

[11] Patent Number: 5,817,108
[45] Date of Patent: Oct. 6, 1998

[54] DEVICE AND METHOD FOR SUTURING WOUND

[75] Inventor: Philippe Poncet, Fremont, Calif.

[73] Assignee: Medtronic, Inc., Minneapolis, Minn.

[21] Appl. No.: 858,782

[22] Filed: May 19, 1997

Related U.S. Application Data

[63] Continuation of Ser. No. 474,613, Jun. 7, 1995, abandoned.

[51] Int. Cl.$^6$ ................................................. A61B 17/00
[52] U.S. Cl. .......................................... 606/139; 606/144
[58] Field of Search .................................. 606/139, 144, 606/148, 145, 147, 185, 187

[56] References Cited

U.S. PATENT DOCUMENTS

| | | | |
|---|---|---|---|
| 4,665,906 | 5/1987 | Jervis | 128/92 YN |
| 5,002,563 | 3/1991 | Pyka et al. | 606/78 |
| 5,219,358 | 6/1993 | Bendel et al. | 606/222 |
| 5,250,055 | 10/1993 | Moore et al. | 606/148 |
| 5,304,184 | 4/1994 | Hathaway et al. . | |
| 5,320,632 | 6/1994 | Heidmueller . | |
| 5,364,408 | 11/1994 | Gordon | 606/144 |
| 5,368,601 | 11/1994 | Sauer et al. | 606/144 |
| 5,374,275 | 12/1994 | Bradley et al. | 606/144 |
| 5,383,882 | 1/1995 | Buess et al. | 606/157 |
| 5,403,328 | 4/1995 | Shallman | 606/144 |
| 5,403,329 | 4/1995 | Hinchcliffe | 606/147 |
| 5,417,699 | 5/1995 | Klein et al. | 606/144 |
| 5,462,561 | 10/1995 | Voda | 606/144 |
| 5,468,251 | 11/1995 | Buelna | 606/223 |
| 5,470,338 | 11/1995 | Whitfield et al. | 606/144 |
| 5,474,568 | 12/1995 | Scott | 606/144 |
| 5,478,353 | 12/1995 | Yoon | 606/213 |
| 5,486,183 | 1/1996 | Middleman et al. . | |
| 5,496,332 | 3/1996 | Sierra et al. . | |
| 5,507,744 | 4/1996 | Tay et al. . | |
| 5,527,321 | 6/1996 | Hinchliffe . | |
| 5,527,322 | 6/1996 | Klein et al. . | |
| 5,540,704 | 7/1996 | Gordon et al. . | |
| 5,540,705 | 7/1996 | Meade et al. . | |
| 5,578,044 | 11/1996 | Gordon et al. | 606/139 |
| 5,591,179 | 1/1997 | Edelstein . | |
| 5,601,572 | 2/1997 | Middleman et al. . | |

FOREIGN PATENT DOCUMENTS

| | | |
|---|---|---|
| 0634141 | 1/1995 | European Pat. Off. . |

OTHER PUBLICATIONS

U.S. Patent Application Serial No. 08/432,305 filed on May 1, 1995 by Nehemiah.

Primary Examiner—Michael Powell Buiz
Assistant Examiner—Kevin Truong
Attorney, Agent, or Firm—Sheldon & Mak

[57] ABSTRACT

A surgical device for suturing a wound in the tissue of a patient. The device includes a longtiudinal sheath having a proximal end and a distal end, a recess formed in the wall of the sheath toward the distal end, a needle constructed of a spring-like material, a retaining mechanism that constrains the needle in a retracted position by deforming the needle, and an actuator at the proximal end of the sheath that releases the restraining mechanism to allow the needle to assume an undeformed condition and move to an exposed position. The needle is movable from the retracted position, where the needle is withdrawn into the recess, to the exposed position, where the needle extends from the recess and points generally in the direction of the proximal end of the device.

46 Claims, 4 Drawing Sheets

DEVICE AND METHOD FOR SUTURING WOUND

This is a continuation of application Ser. No. 08/474,613 filed on Jun. 7, 1995 now abandoned.

This invention relates to a surgical instrument for closing the edges of a wound together with surgical sutures.

BACKGROUND OF THE INVENTION

Minimum invasive surgery generally includes the creation of trocar puncture wounds through the abdominal wall of a patient for insertion of a variety of surgical instruments. The structural strength of the abdominal wall is derived mostly from one or more layers of fascia disposed beneath the skin and between layers of muscle. Unless closed properly, the abdominal contents may herniate through these wounds, or body fluids can accumulate, promoting infection. Presently, surgeons attempt to close trocar puncture wounds using conventional needle drivers which are often cumbersome, making it difficult to properly close the wound.

Larger trocars (10 mm and larger) are commonly used for surgical procedures. For large trocars and to avoid potential hernias, it is desirable to utilize flexible threads, or sutures, passing through apposing tissue edges tied to hold the more deeply buried portions of the edge of the wound together. Attempts have been made to address these problems, for example, in U.S. Pat. No. 5,368,601 to Sauer et al; U.S. Pat. No. 5,374,275 to Bradley et al; and European Patent Application No. 0 634 141. However, these devices employ multiple needles, which result in a complex device which is complicated in use and expensive to manufacture.

U.S. Pat. No. 5,403,328 to Shallman describes a surgical apparatus for closing a trocar incision. The Shaliman device includes a curved needle pivotally positioned within a casing. The mechanism for pivoting the needle of Shallman is somewhat cumbersome, even while deflection of the needle is limited, and requires a long stroke to manipulate the needle.

SUMMARY OF THE INVENTION

The present invention is a simple instrument for closing trocar incision sites and delivering sutures. The present invention is a needle assembly in which the needle is constructed of a spring-like material and initially housed within a sheath in a deformed condition. The needle can be easily exposed by sliding an actuator so as to release constraining means and allow the needle to assume its undeformed condition. The needle assembly has few parts, allows a wide range for deflection of the needle, and the needle may be exposed with a relatively short stroke.

A first aspect of the invention comprises a surgical device for suturing a wound in the tissue of a patient comprising:
  a sheath having a longitudinal axis including a proximal end and a distal end;
  a recess formed in the wall of the sheath toward the distal end;
  a needle constructed of a spring-like material, the needle being movable from a first retracted position wherein the needle is withdrawn into the recess to a second exposed position wherein the needle is extended from the recess;
  means for constraining the needle in its retracted position by deforming the needle;
  an actuator at the proximal end of the sheath for releasing the constraining means, so as to thereby allow the needle to assume its undeformed condition and move to the exposed position;
  the needle having a configuration such that upon extension from the distal end of the sheath, the needle points in the direction of the proximal end.

A further aspect of the invention comprises a surgical device for suturing a wound in the tissue of a patient comprising:
  a sheath having a longitudinal axis including a proximal end and a distal end;
  a recess formed in the wall of the sheath toward said distal end;
  a needle constructed of a shape memory alloy material comprising a generally S-shape and including a body having one end fixedly attached to the interior of the distal end of the sheath, the body of the needle being movable in the sheath from a first position wherein the needle is retracted into the recess to a second position exposed wherein the needle is extended laterally from the recess;
  means for constraining the needle in the first position.
  an actuator at the proximal end of the sheath for releasing the constraining means, the actuator comprising:
    a sleeve slidable within the sheath;
    an opening formed in the distal end of the sleeve through which the needle extends in the exposed position;
    wherein the means for constraining comprises a section of the sleeve formed between the opening and the distal end of the actuator such that upon release of the means for constraining the needle moves to the second, exposed position;
  the needle having a configuration such that upon extension from the distal end of the sheath, the needle points in the direction of the proximal end.

DETAILED DESCRIPTION OF THE PREFERRED EMBODIMENT

Figure 1:
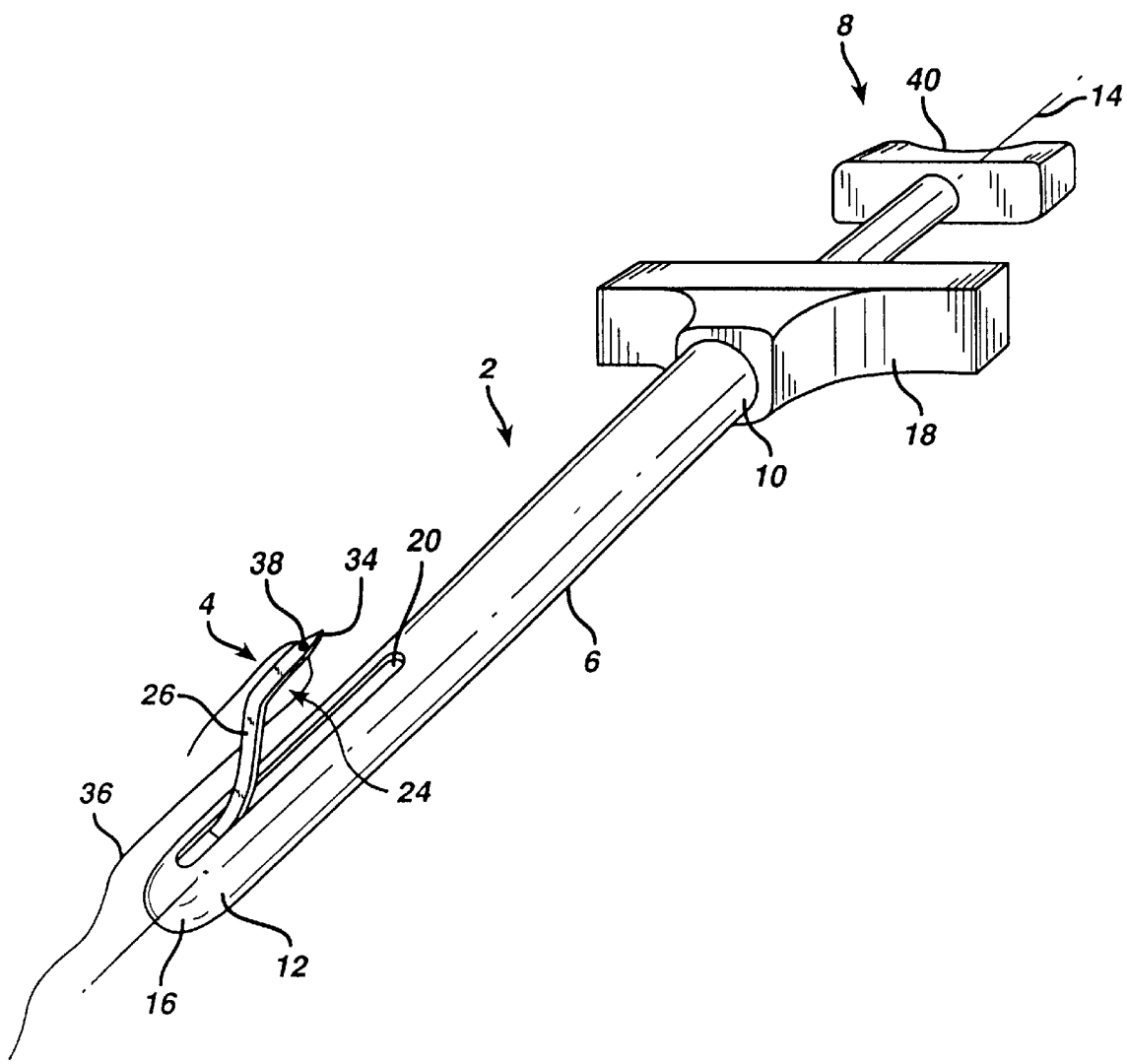
FIG. 1 is a perspective view of the present invention.
Figure 3A:
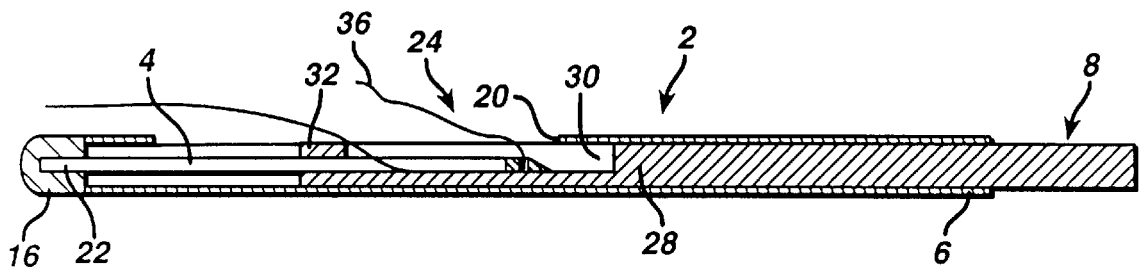
FIGS. 3a, 3b and 3c are schematic views of deployment of the present invention.

Referring now to the drawings, FIG. 1 illustrates a surgical device in the form of a puncture closure device 2 including a needle 4 movable in sheath 6. An actuator 8 is capable of moving needle 4 from a first, retracted position, as seen in FIG. 3a, to a second, exposed position, as seen in FIGS. 1 and 3c. Device 2 is designed to be used in a sterile surgical field. The device may be disposable or reusable or partially disposable or reusable. The outer radial dimension of device 2 is 10 mm or less.

Sheath 6 is a tubular sheath having a proximal end 10 and a distal end 12 disposed along opposite ends of longitudinal axis 14. Sheath 6 includes a blunt tip 16 located at the distal end and a gripping section 18 located at the proximal end. The advantage of a blunt end is to eliminate risk of inadvertent puncture of organs or tissue when inserting the device into a wound. A recess 20 is formed in the wall of the sheath adjacent to blunt tip 16 through which needle 4 may be extended, as seen in the Figures and as discussed below.

Needle 4 includes a body having a generally S-shaped configuration. A first end 22 of needle 4 is fixedly attached to the interior of the distal end of the sheath. Needle 4 may be fixedly attached to sheath 6 at end 22 by pins or other mechanical attachment, or may be formed with the sheath. The end opposite first end 22 of needle 4 is manipulation end 24, which includes a straightened portion 26. It should be noted, however, that the manipulation end may include a curved portion, rather than straightened portion 26. Needle 4 is constructed of a spring-like material. In its undeformed configuration, needle 4 assumes its S-shaped configuration exposed so that the S-shape extends from fixed end 22 through recess 20 to manipulation end 24. Straightened portion 26 is then generally parallel to longitudinal axis 14. In its deformed configuration, the needle is confined within recess 20. Needle 4 moves from its retracted position to its exposed position by operation of actuator 8. When manipulation end 24 is retracted within recess 20, puncture closure device 2 is in its retracted position. When the manipulation end is extended from recess 20, the puncture closure device is in the exposed position.

As discussed above, needle 4 may be constructed of a spring-like material, such as a shape memory alloy or stainless steel. The requirements are that the material be sufficiently resilient and bio-compatible. However, the needle is preferably constructed of a shape memory alloy, more preferably of superelastic material, and most preferably of an alloy including nickel titanium. With shape memory alloys, the radius of curvature of the S-shape can be smaller than with conventional materials, thereby permitting construction of a needle which has a configuration in which the manipulation end of the needle may be a greater distance from the sheath and in which the length of the S-shaped needle may be shorter.

Actuator 8 includes a sleeve 28 slidable within sheath 6. The proximal portion of the sleeve may be solid or rod-like, or may be substantially hollow. Sleeve 28 includes an opening 30 formed adjacent to the distal end of the sleeve, leaving a section of sleeve 32 between the distal tip of the sleeve and its opening 30. Section 32 forms a ring-shaped portion encircling needle 4 which extends from distal end 12 of the sheath, through the distal tip of the sleeve. In its initial state, section 32 is positioned on manipulation end 24 so as to deform needle 4, thereby constraining the needle in recess 20 in its retracted position. As actuator 8 is deployed, sleeve 28 slides toward the distal end of sheath 6, releasing the needle from section 32 and allowing needle 4 to assume its undeformed S-shaped configuration, thereby exposing the needle for use. In this position, manipulation end 24 extends through opening 30, as well as through recess 20. Device 2 may be returned to its initial state by sliding actuator 8 within sheath 6. With an actuation arrangement as described in the present invention, the device can be actuated with a short longitudinal stroke. A stop having cooperating surfaces on actuator 8 and sheath 6 prevents the actuator from being accidentally withdrawn completely from the sheath.

Manipulation end 24 of needle 4 terminates in a sharp point 34. Manipulation end 24 includes means for slidably receiving and retaining a suture 36. The means for slidably receiving and retaining suture 36 may be in the form of a hole 38, as seen in the Figures. or a notch, not shown. The hole or notch is sized to accommodate sutures of varying diameters. In any of these embodiments, sharp point 34 is capable of piercing the tissue adjacent to the patient's wound when extended by actuator 8.

A thumb grip 40 is disposed at the proximal end of sleeve 8 for actuating in conjunction with gripping sections 18 of sheath 6.

Figure 3B:
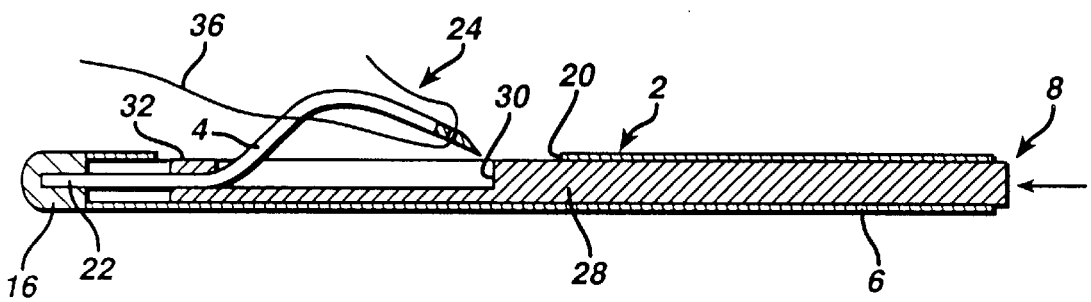
Figure 3C:
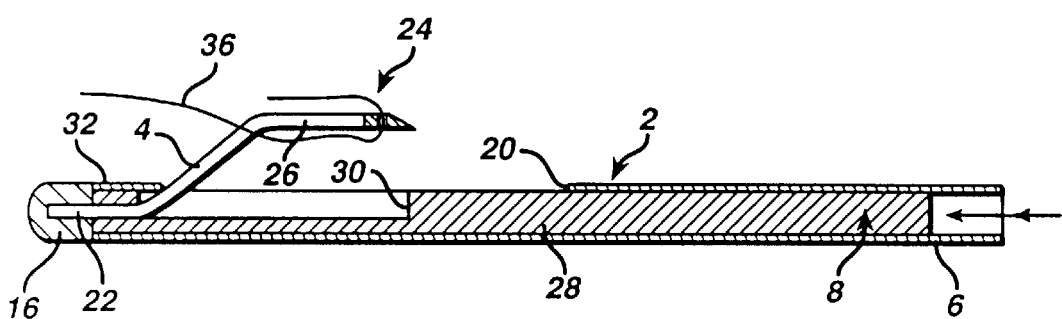

In operation, puncture closure device 2 is introduced into a wound with suture 36 attached, as shown in FIGS. 3, by threading suture 36 through hole 38 or notch) located in the manipulation end of the needle. Device 2 is positioned within the wound such that sharp point 34 is beneath the tissue to be sutured. Actuator 8 is then deployed by holding two fingers beneath gripping section 18 and using thumb grip 40 to push the gripping section and thumb grip relative to each other, so as to move needle 4 from a first position retracted within sheath 6, as seen in FIG. 3a, through an intermediate position as shown in FIG. 3b, to the exposed position as shown in FIG. 3c. However, it is to be understood that any gripping means could be employed for actuating the device, such as pistol grip, scissors action, screw mechanism or plunger mechanism. At this point, sharp point 34 points in the proximal direction, toward actuator 8. Device 2 is pulled upward, through tissue, from the internal layers to the external layers, driving sharp point 34 of needle 4 and suture 36 through one edge of the tissue surrounding the wound. A first portion of suture 36 is pulled through the tissue. The device may be temporarily returned to the intermediate position shown in FIG. 3b to facilitate suture retrieval from the wound edge. Device 2 is then pushed back through the tissue in the direction from external tissue to internal tissue, such that the needle is no longer piercing any tissue. Suture 36 is still attached to needle 4. Device 2 is rotated within the wound. The device is again pulled upward, through the opposite edge of tissue, from internal layers to external layers, such that the other tissue edge of the wound is pierced with the sharp point of the needle, pulling the other end of suture 36 through the tissue. The device may be again temporarily returned to its intermediate position as seen in FIG. 3b. Suture 36 is removed from the needle, such that suture 36 is now completely free from device 2. Needle 4 is pushed back through the pierced tissue in the direction from external tissue to internal tissue, fully through the internal layer so that the sharp point of the needle is not piercing any tissue. Needle 4 may be returned to its retracted position such that section 32 of sleeve constrains the needle. Device 2 is fully withdrawn from the wound. Suture 34 is tied. The specific positions of FIGS. 3a, 3b and 3c may be determined by any suitable means, for example a detent between the sheath and the sleeve.

Figure 2:
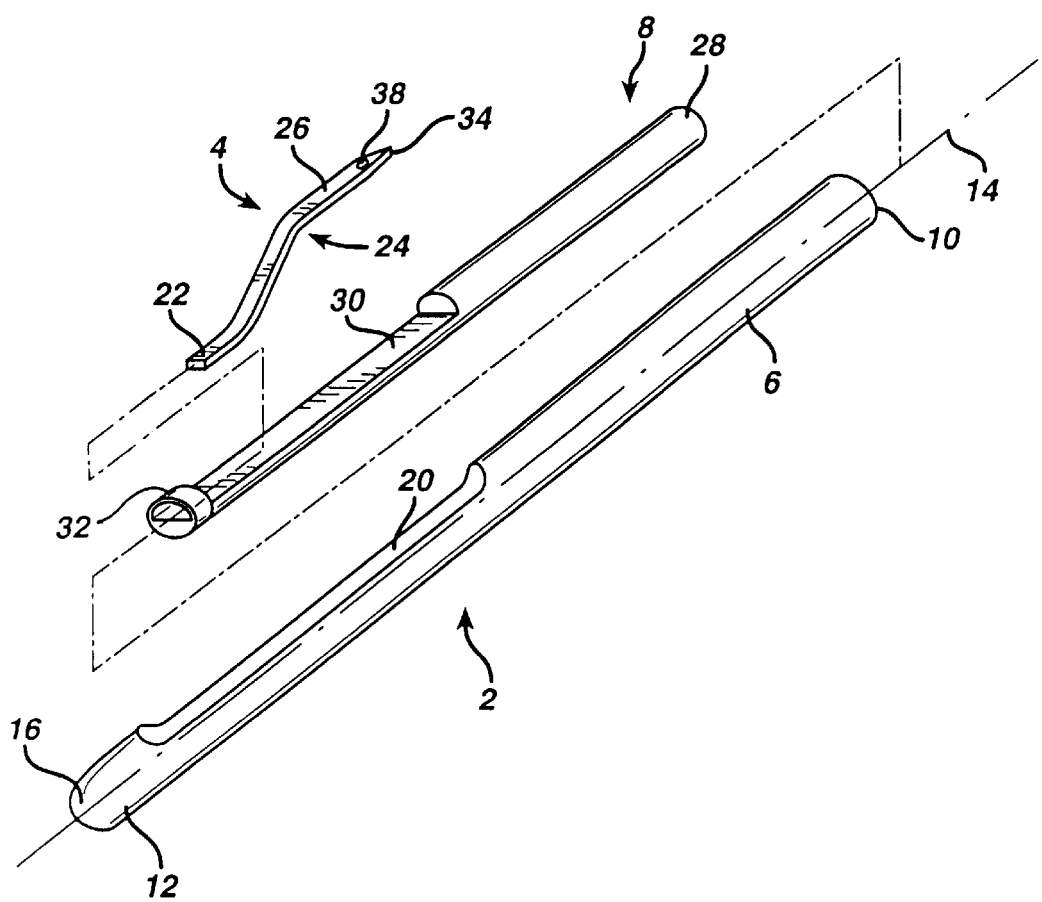
FIG. 2 is an exploded view of the device of FIG. 1.
Figure 4A:
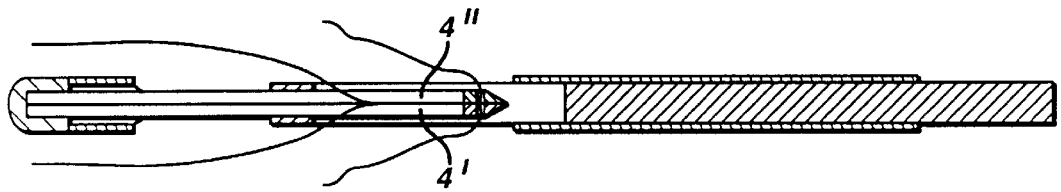
FIGS. 4a, 4b and 4c are schematic views of a second embodiment of the present invention.
Figure 4B:
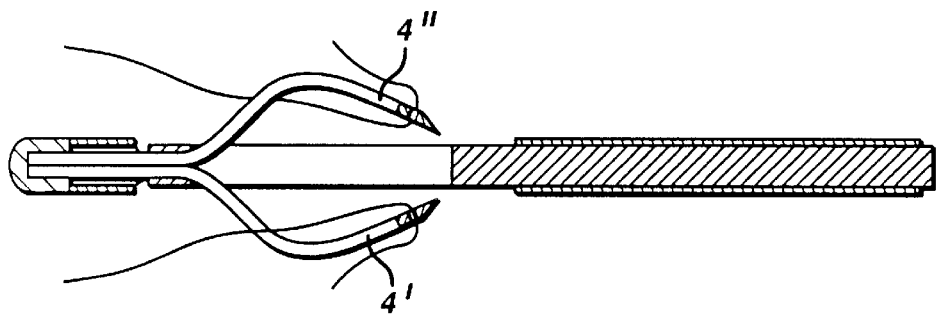
Figure 4C:
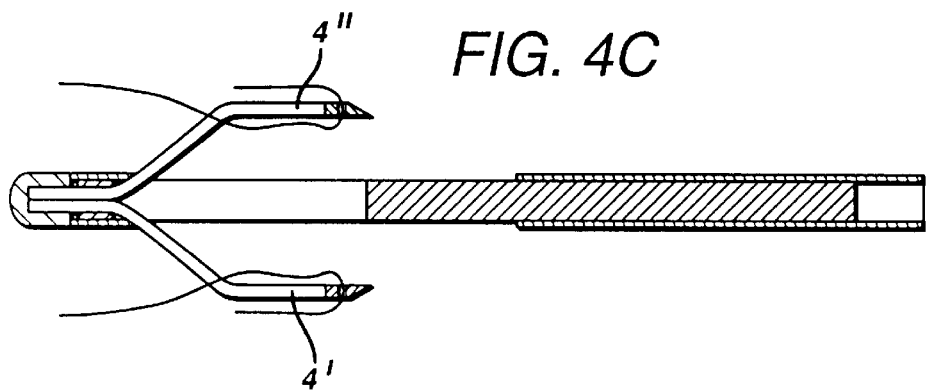

Device 2 may be constructed with double needles, as shown in FIGS. 4a–4c. FIG. 4a illustrates double needles 4', 4" in the retracted position, moving through an intermediate position shown in FIG. 4b to FIG. 4c, which illustrates needles 4', 4" in the exposed position. Actuation of the device may be achieved by a single actuator, as described above, or with the use of dual sleeves. Operation of the device is generally the same as that described in connection with the embodiment of FIGS. 1–3.

While the needle is described as being fixed to the sheath, it is within the scope of this invention to construct the device with the needle fixed to the distal end of the actuator, rather than the sheath. Variations and modifications can be made to the present invention without departing from the scope of the present invention, which is limited only by the following claims.

I claim:

1. A surgical device for suturing a wound in the tissue of a patient comprising:

a sheath having a longitudinal axis including a proximal end and a distal end;

a recess formed in the wall of said sheath toward said distal end;

a needle constructed of a spring-like material, said needle having a fixed end non-movably attached to the interior of said distal end of said sheath, and said needle being movable from a first retracted position wherein said needle is withdrawn into said recess to a second generally undeformed exposed position wherein said needle is extended from said recess;

a restraining mechanism for constraining said needle in the first retracted position by elastically deforming said needle;

an actuator at said proximal end of said sheath for releasing said restraining mechanism, so as to thereby allow said needle to assume an undeformed condition and move to said second exposed position;

said needle having a configuration such that upon extension from said distal end of said sheath, said needle points generally in the direction of said proximal end.

2. The surgical device as defined in claim 1 wherein said spring-like material is a shape memory alloy.

3. The surgical device as defined in claim 2 wherein said shape memory alloy is superelastic.

4. The surgical device as defined in claim 2 wherein said shape memory alloy is made from an alloy including nickel titanium.

5. The surgical device as defined in claim 1 wherein one end of said needle is fixedly attached to the interior of the distal end of said sheath.

6. The surgical device as defined in claim 1 wherein said actuator comprises:
a sleeve slidable within said sheath;
an opening formed in the distal end of said sleeve through which said needle extends in the exposed position;
wherein said restraining mechanism comprises a section of said sleeve formed between said opening and the distal end of said actuator.

7. The surgical device as defined in claim 1 wherein in the exposed position, said needle extends outwardly of said sheath.

8. The surgical device as defined in claim 1 wherein in the exposed position, said needle is spaced from the longitudinal axis of said sheath.

9. The surgical device as defined in claim 1 wherein said needle has an S-shaped undeformed configuration.

10. The surgical device as defined in claim 9 further including a straightened portion at a manipulation end of said needle such that said manipulation end is generally parallel to the longitudinal axis of said sheath.

11. The surgical device as defined in claim 1 wherein said sheath includes a blunt tip.

12. The surgical device as defined in claim 1 wherein said device includes a pair of needles.

13. The surgical device as defined in claim 1 further comprising means for receiving a suture.

14. The surgical device of claim 1 wherein the movement of the needle from the first retracted position to the second exposed position occurs at body temperature of the patient.

15. A surgical device for suturing a wound in the tissue of a patient comprising:
a sheath having a longitudinal axis including a proximal end and a distal end;
a recess formed in the wall of said sheath toward said distal end;
a needle constructed of a shape memory alloy material comprising a generally S-shape and including a body and having one end fixedly attached to the interior of the distal end of said sheath, the body of said needle being movable in said sheath from a first position wherein said needle is retracted into said recess to a second position exposed wherein said needle is extended laterally from said recess;
means for constraining said needle in said retracted first position;
an actuator at said proximal end of said sheath for releasing said constraining means, said actuator comprising:
a sleeve slidable within said sheath;
an opening formed in the distal end of said sleeve through which said needle extends in the exposed position;
wherein said means for constraining comprises a section of said sleeve formed between said opening and the distal end of said actuator such that upon release of said means for constraining said needle moves to said second, exposed position;
said needle having a configuration such that upon extension from said distal end of said sheath, said needle points in the direction of said proximal end.

16. The surgical device as defined in claim 15 wherein said needle is in a deformed condition in the retracted position and assumes its undeformed condition in the exposed position.

17. The surgical device as defined in claim 15 wherein said body of said needle includes a straightened portion at a manipulation end of said needle such that said manipulation end of said needle is generally parallel to the longitudinal axis of said sheath in said exposed position.

18. The surgical device as defined in claim 15 wherein said sheath includes a blunt tip.

19. The surgical device as defined in claim 15 wherein said device includes a pair of needles.

20. The surgical device as defined in claim 15 further comprising means for receiving a suture.

21. A surgical device for suturing a wound in the tissue of an individual, the surgical device comprising:
a) a housing including a proximal end, a distal end, a wall defining a chamber, and an opening formed in the wall at the distal end in communication with the chamber;
b) a needle having (i) an undeformed configuration, and (ii) a deformed configuration; and
c) means movably disposed within the chamber for selectively restraining the needle in the deformed configuration within the chamber and for causing the needle to transform from the deformed configuration to the undeformed configuration and to extend exteriorly of the housing through the opening.

22. A surgical device for suturing a wound in the tissue of an individual, the surgical device comprising:
a) a housing including a proximal end, a distal end, a wall defining a chamber, and an opening formed in the wall at the distal end in communication with the chamber;
b) a needle having (i) an undeformed configuration, and (ii) a deformed configuration; and
c) a restraint movably disposed within the chamber, the restraint being selectively positionable (i) to maintain the needle in the deformed configuration within the chamber, and (ii) to cause the needle to transform at body temperature from the deformed configuration to the undeformed configuration and to extend exteriorly of the housing through the opening.

23. The surgical device as defined in claim 22 wherein the restraint is movable within the chamber (i) in a first direction so as to cause the needle to transform from the undeformed configuration to the deformed configuration, and (ii) in a second direction so as to transform the needle from the deformed configuration to the undeformed configuration.

24. The surgical device as defined in claim 22 wherein the restraint comprises a body including a ring-shaped portion at one end of the body, the ring-shaped portion defining an axial passage through which the needle extends.

25. The surgical device as defined in claim 22 wherein the needle is comprised of a material capable of repeatedly transforming between the undeformed configuration and the deformed configuration in response to repeated movement of the restraint within the chamber.

26. The surgical device as defined in claim 22 wherein the needle is comprised of a shape memory alloy.

27. The surgical device as defined in claim 22 wherein the housing has a longitudinal axis and the needle comprises a straight portion which extends in the undeformed configuration generally parallel to the longitudinal axis toward the proximal end of the housing.

28. The surgical device as defined in claim 27 wherein the straight portion of the needle includes means for retaining a suture.

29. A surgical device for suturing a wound in the tissue of an individual, the surgical device comprising:
   a) a housing sized for removable insertion into the wound, the housing including a proximal end, a distal end, a wall defining a chamber, and an opening formed in the wall at the distal end in communication with the chamber;
   b) a needle comprised of a superelastic alloy, the needle having (i) an undeformed configuration, and (ii) a deformed configuration in which a mechanical stress is applied to the needle, wherein the needle transforms from the deformed configuration to the undeformed configuration in response to the release of the stress from the needle;
   c) a restraint disposed to apply a mechanical stress to the needle so as to maintain the needle in the deformed configuration within the chamber; and
   d) an actuator selectively movable within the chamber to move the restraint so as to release the mechanical stress from the needle, thereby causing the needle to transform to the undeformed configuration and to extend exteriorly of the housing through the opening in the wall.

30. The surgical device as defined in claim 29 wherein the actuator is movable within the chamber (i) in a first direction to cause the restraint to apply the mechanical stress to the needle, thereby transforming the needle from the undeformed configuration to the deformed configuration, and (ii) in a second direction to cause the restraint to release the mechanical stress applied to the needle, thereby transforming the needle from the deformed configuration to the undeformed configuration.

31. The surgical device as defined in claim 29 wherein the needle is disposed entirely within the chamber of the housing in the deformed configuration, and the needle is disposed partially within the chamber in the undeformed configuration.

32. The surgical device as defined in claim 29 wherein the restraint comprises a portion of the actuator.

33. The surgical device as defined in claim 29 wherein the housing defines a longitudinal axis and the needle comprises a straight portion which in the undeformed configuration is disposed exterior to the housing and extends generally parallel to the longitudinal axis toward the proximal end.

34. The surgical device as defined in claim 29 wherein the needle has (i) a straight deformed configuration, and (ii) an S-shaped undeformed configuration.

35. A surgical device for suturing a wound in the tissue of an individual, the surgical device comprising:
   a) a housing sized for removable insertion into the wound, the housing including a wall defining a chamber, and an opening formed in the wall in communication with the chamber;
   b) a needle comprised of a resilient material, the needle having (i) an undeformed configuration, and (ii) a deformed configuration in which a mechanical stress is applied to the needle, wherein the needle transforms from the deformed configuration to the undeformed configuration in direct response to the release of the mechanical stress from the needle;
   c) means for non-movably attaching an end of the needle to the housing;
   d) a restraint disposed to apply a mechanical stress to the needle so as to maintain the needle in the deformed configuration within the chamber; and
   e) an actuator selectively movable within the chamber to cause the restraint to release the mechanical stress from the needle, thereby causing the needle to transform from the deformed configuration to the undeformed configuration and to extend exteriorly of the housing through the opening in the wall.

36. The surgical device as defined in claim 35 wherein the needle is comprised of a shape memory alloy which repeatedly transforms between the deformed configuration and the undeformed configuration in response to repeated movement of the actuator within the chamber.

37. A surgical device for suturing a wound in the tissue of an individual, the surgical device comprising:
   a) a housing for insertion into the wound, the housing including a proximal end, a distal end, a wall defining a chamber, and a pair of openings formed in the wall at the distal end in communication with the chamber;
   b) a pair of needles each having (i) an undeformed configuration, and (ii) a deformed configuration in which a mechanical stress is applied to the needles, wherein the needles transform from the deformed configuration to the undeformed configuration in response to the release of the mechanical stress from the needles; and
   c) a restraint movably disposed in the chamber (i) to apply a mechanical stress to the needles so as to maintain the needles in the deformed configuration within the chamber, and (ii) to release the mechanical stress from each of the needles, thereby causing the needles to transform to the undeformed configuration and to each extend exteriorly of the housing through one of the openings in the wall.

38. The surgical device as defined in claim 37 wherein the needles are each comprised of a shape memory alloy which repeatedly transforms between the deformed configuration and the undeformed configuration in response to repeated movement of the restraint within the chamber.

39. The surgical device as defined in claim 37 wherein the needles each include a fixed end, the surgical device further comprises means for non-movably attaching the fixed ends of the needles to the housing.

40. The surgical device as defined in claim 37 wherein the needles each have (i) a straight deformed configuration and (ii) an S-shaped undeformed configuration, the housing defines a longitudinal axis and the needles each comprise a straight portion which in the undeformed configuration is disposed exterior to the housing and extends generally parallel to the longitudinal axis toward the distal end.

41. A surgical device for suturing a wound in the tissue of an individual, the surgical device comprising:

a) an elongated housing for insertion into the wound, the housing including a wall defining a longitudinal bore and an opening formed in the wall in communication with the longitudinal bore;

b) a needle comprised of a superelastic alloy, the needle having (i) a generally S-shaped, undeformed configuration, and (ii) a deformed configuration generally corresponding to the shape of the longitudinal bore, wherein the needle transforms from the undeformed configuration to the deformed configuration by application of a mechanical stress to the needle, and the needle transforms from the deformed configuration to the undeformed configuration in direct response to the release of the mechanical stress;

c) a restraint disposed to apply a mechanical stress to a portion of the needle to maintain the needle in the deformed configuration within the longitudinal bore; and d) an actuator movable within the longitudinal bore to move the restraint relative to the needle so as to release the mechanical stress from the portion of the needle, thereby causing the needle to transform from the deformed configuration to the undeformed configuration and to extend exteriorly of the housing through the opening in the wall.

42. A method of suturing a wound, comprising the steps of:

(a) inserting a surgical device as defined in claim 22 into the wound with the needle in the deformed configuration;

(b) moving the restraint within the chamber of the housing to transform the needle from the deformed configuration to the undeformed configuration such that the needle extends exteriorly of the housing through the opening in the wall, the needle having an attached suture;

(c) suturing the wound using the surgical device; and (d) withdrawing the surgical device from the wound.

43. The method as defined in claim 42 further comprising prior to the step of withdrawing, the step of moving the restraint within the chamber of the housing to withdraw the needle through the opening and into the chamber such that the needle transforms to the deformed configuration.

44. The method as defined in claim 42 wherein the needle is comprised of a superelastic material.

45. The method as defined in claim 42 wherein the housing defines a longitudinal axis and the needle comprises a straight portion which in the undeformed configuration is disposed exterior to the housing and extends generally parallel to the longitudinal axis toward the proximal end of the housing.

46. The method as defined in claim 42 wherein the needle has (i) a straight deformed configuration and (ii) an S-shaped undeformed configuration including a straight portion having a pointed end, the straight portion is disposed exterior to the housing and extends toward the proximal end in the undeformed configuration.

* * * * *